United States Patent
Halwani et al.

(10) Patent No.: US 9,655,847 B1
(45) Date of Patent: May 23, 2017

(54) THERAPEUTIC LIPOSOME AND METHOD OF TREATING A SUBJECT HAVING CANCER

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Majed Abdulaziz Saleh Halwani, Riyadh (SA); Moayad Abdulaziz Alhariri, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 0 days.

(21) Appl. No.: 15/212,389

(22) Filed: Jul. 18, 2016

(51) Int. Cl.
*A61K 9/127* (2006.01)
*A61K 31/704* (2006.01)

(52) U.S. Cl.
CPC .......... *A61K 9/127* (2013.01); *A61K 31/704* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| 5,731,346 A * | 3/1998 | Egberg | A61K 31/20 514/458 |
| 2002/0146448 A1* | 10/2002 | Kozbor | A61K 9/127 424/450 |
| 2007/0116753 A1* | 5/2007 | Hong | A61K 9/0019 424/450 |
| 2011/0274746 A1* | 11/2011 | Schmidt | A61K 9/127 424/450 |
| 2012/0076795 A1 | 3/2012 | Debs | |
| 2012/0288558 A1* | 11/2012 | Gabizon | A61K 31/337 424/450 |

(Continued)

FOREIGN PATENT DOCUMENTS

| EP | 0 198 765 A2 | 10/1986 |
| EP | 0 198 765 A3 | 10/1986 |
| WO | WO 2011/143271 A2 | 11/2011 |

OTHER PUBLICATIONS

PG Rose. "Pegylated Liposomal Doxorubicin: Optimizing the Dosing Schedule in Ovarian Cancer." The Oncologist, vol. 10, 2005, pp. 205-214.*

(Continued)

*Primary Examiner* — Isaac Shomer
(74) *Attorney, Agent, or Firm* — Oblon, McClelland, Maier & Neustadt, L.L.P.

(57) ABSTRACT

A therapeutic liposome including a bilayer comprising at least one poly-unsaturated fatty acid (omega-3 fatty acid, omega-6 fatty acid, and omega-9 fatty acid), a beta-glucan, a cholesterol, and a doxorubicin. The liposome has a diameter of 100 nm to 1.5 μm. The beta-glucan and the doxorubicin are encapsulated in the liposome and the cholesterol is integral to the bilayer of the liposome.

13 Claims, 5 Drawing Sheets

(56) References Cited

U.S. PATENT DOCUMENTS

2013/0022663 A1    1/2013  Buckman

OTHER PUBLICATIONS

Janssen Inc. "Product Monograph Caelyx®." Janssen Inc., Revised Oct. 10, 2013, pp. 1-55.*
D Akramiene, A Kondrotas, J Didziapetriene, E Kevelaitis. "Effects of b-glucans on the immune system." Medicina (Kaunas), vol. 43(8), 2007, pp. 597-606.*
Majed Halwani, et al., "Liposomal β-Glucan: Preparation, Characterization and Anticancer Activities", Journal of Nanomedicine & Nanotechnology, vol. 6, Issue 5, Oct. 2015, 7 pages.
Godfrey Chi-Fung Chan., et al., "The effects of β-glucan on human immune and cancer cells", Journal of Hematology & Oncology 2:25, pp. 1-11, (2009).

* cited by examiner

THERAPEUTIC LIPOSOME AND METHOD OF TREATING A SUBJECT HAVING CANCER

BACKGROUND OF THE INVENTION

Technical Field

The present invention relates to a liposome for treating cancer by including doxorubicin, a polyunsaturated fatty acid, and beta glucan in combination.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Doxorubicin (DOX) has been found to have a broad spectrum of application in cancer, which includes numerous solid tumors such as breast cancer, sarcomas and bladder cancers. See Weinstein D M, Mihm M J, Bauer J A. "Cardiac peroxynitrite formation and left ventricular dysfunction following doxorubicin treatment in mice," *J Pharmacol Exp Ther* 2000; 294: 396-401, incorporated herein by reference in its entirety. Despite its common use, the clinical utility of DOX is compromised by dose-limiting cardiotoxicity due to its effects on mitochondria. The heart contains a large amount of energy producing mitochondria to function as a pump which requires a great amount of energy that circulates blood throughout the body. See Angsutararux P, Luanpitpong S, Issaragrisil S. "Chemotherapy-Induced Cardiotoxicity: Overview of the Roles of Oxidative Stress," *Oxid Med Cell Longev* 2015; 2015: 795602, incorporated herein by reference in its entirety. A mitochondrion is the site of most reactive oxygen species (ROS) which are produced as a result of electrons escaping from electron transport chain and captured by oxygen, rendering it as a main source of superoxide production. See Andreyev A Y, Kushnareva Y E, Murphy A N et al. "Mitochondrial ROS Metabolism: 10 Years Later," *Biochemistry (Most)* 2015; 80: 517-31, incorporated herein by reference in its entirety. However, DOX can drive these ROS production to much higher levels. See Varin R, Mulder P, Richard V et al. "Exercise improves flow-mediated vasodilatation of skeletal muscle arteries in rats with chronic heart failure. Role of nitric oxide, prostanoids, and oxidant stress," *Circulation* 1999; 99: 2951-7. Recent research suggests that nitric oxide (NO) may play diverse roles in cardiac function and disease. High level of NO production is associated with multiple forms of cardiac disease, including dilated cardiomyopathy and congestive heart failure. See Fadillioglu E, Yilmaz H R, Erdogan H et al. The activities of tissue xanthine oxidase and adenosine deaminase and the levels of hydroxyproline and nitric oxide in rat hearts subjected to doxorubicin: protective effect of erdosteine. *Toxicology* 2003; 191: 153-8, incorporated herein by reference in its entirety. A mechanism to reduce cardiotoxicity from DOX is of interest to the medical community.

Glucans are important secondary metabolites isolated from plants and micro-organisms. Glucans are generally described as a polysaccharide of D-glucose monomers, linked by glycosidic bonds. They exhibit prophylactic and therapeutic properties, and can function as biological response modifiers when administered to mammals. As such, glucans have shown beneficial effects in the treatment of infectious and autoimmune diseases, and in clinical management of cancer.

Glucans target various cell types in the immune system, and more particularly macrophages. Previous research has shown that glucans display protective properties against experimentally induced infections in mammalian model systems. Specifically, glucans exert their function on macrophages, monocytes, lymphocytes, and other immune cells in the mammalian system that plays a significant role in elicitation of the immune response.

For example, administration of glucans has been shown to significantly enhance the immune system in animals to a wide variety of experimentally induced bacterial, viral, fungal and parasitic infections. Glucans also show strong anti-tumor activity. Glucan carries out its biological function by binding to specific receptor molecules located on the surface of macrophages. In in vitro studies, exposure of these cells to beta-glucans stimulates the immune system. One representative glucan with such immune-enhancing characteristics is branched beta (1,3)-glucan.

Beta-glucans are naturally occurring polymers of saccharides (polysaccharides) and are constituents of the cell wall of certain pathogenic bacteria, algae, fungi, and cereals (e.g. oats, barley, rye, wheat). The healing and immunostimulating properties of mushrooms have been known for thousands of years in the Eastern countries. These mushrooms contain biologically active polysaccharides that mostly belong to group of beta-glucans. Beta-glucans can increase host immune defense by enhancing macrophages and natural killer cell function. The induction of cellular responses by beta-glucans is likely to involve their specific interaction with several cell surface receptors, such as complement receptor 3 (CR3; CD11b/CD18), lactosylceramide, selected scavenger receptors, and dectin-1 (betaGR). As an immunostimulating agent, which acts through the activation of macrophages and NK cell cytotoxicity, beta-glucan can inhibit tumor growth in promotion stage also. The interaction between glucan and its receptor produce further stimulatory effects such as enhanced phagocytosis, increased cell size, enhanced cell proliferation, enhanced adherence and chemotactic activity and production of a wide range of cytokines and leukotrienes.

Cytokines are critical to a myriad of fundamental homeostatic and pathophysiological processes such as fever, wound healing, inflammation, tissue repair and fibrosis. They play important roles in regulating cell function such as proliferation, migration, and matrix synthesis. It is the balance or the net effect of the complex interplay between these mediators, which appears to play a major role in regulating the initiation, progression and resolution of wounds. Wound healing involves a complex process including induction of acute inflammation by the initial injury, followed by parenchymal and mesenchymal cell proliferation, migration, and activation with production and deposition of extracellular matrix.

A study reported that β-glucan has immunomodulation effect on innate and adaptive immunity. See Thompson I J, Oyston P C, Williamson D E. "Potential of the beta-glucans to enhance innate resistance to biological agents," *Expert Rev Anti Infect Ther* 2010; 8: 339-52, incorporated herein by reference in its entirety. β-glucan react on immune receptors such as dectin-1 to trigger cell response including monocytes, macrophages, neutrophils, natural killer cells and dendritic cells. See Fang J, Wang Y, Lv X et al. "Structure of a beta-glucan from *Grifola frondosa* and its antitumor effect by activating Dectin-1/Syk/NF-kappaB signaling,"

*Glycoconj J* 2012; 29: 365-77; Lee S Y, Lee Y G, Byeon S E et al. "Mitogen activated protein kinases are prime signalling enzymes in nitric oxide production induced by soluble beta-glucan from *Sparassis crispa*," *Arch Pharm Res* 2010; 33: 1753-60, each incorporated herein by reference in its entirety. As a consequence of activation of dectin-1 signaling pathway, cytokines including interleukin IL-12, IL-6, IL-10 and tumor necrosis factors are released. These cytokines might play a major role in the cancer therapy uses for β-glucan. See Chan G C, Chan W K, Sze D M. "The effects of beta-glucan on human immune and cancer cells," *J Hematol Oncol* 2009; 2: 25, incorporated herein by reference in its entirety, which describes Maitake D-Fraction extracted from *Grifola frondosa* (Maitake mushroom) was found to decrease the size of the lung, liver and breast tumors in >60% of patients when it was combined with chemotherapy in a 2 arms control study comparing with chemotherapy alone (page 8, right column, lines 1-5). Previous studies showed that β-glucan increased cytotoxicity and synergized with a specific anti-tumor monoclonal antibody in killing tumor cells. See Cheung N K, Modak S, Vickers A et al. "Orally administered beta-glucans enhance anti-tumor effects of monoclonal antibodies," *Cancer Immunol Immunother* 2002; 51: 557-64, incorporated herein by reference in its entirety. Another study reported the anticancer activity of β-glucan on human dermal cells through induction of caspase-12 expression. See Choromanska A, Kulbacka J, Rembialkowska N et al. Anticancer properties of low molecular weight oat beta-glucan—An in vitro study. *Int J Biol Macromol* 2015; 80: 23-8, incorporated herein by reference in its entirety.

As cancer chemoprevention research has advanced, interest toward investigation of natural products such as omega-3. Several studies demonstrated the beneficial effect of omega-3 as antioxidant, anti-inflammatory and anti-apoptotic agent. Uygur et al. examined administration of omega-3 along with doxorubicin and found that omega-3 protect against DOX acute cardiotoxicity in vivo due to the antioxidant and anti-apoptotic properties. See Zararsiz I, Kus I, Akpolat N et al. "Protective effects of omega-3 essential fatty acids against formaldehyde-induced neuronal damage in prefrontal cortex of rats," *Cell Biochem Funct* 2006; 24: 237-44; Zararsiz I, Sonmez M F, Yilmaz H R et al. "Effects of omega-3 essential fatty acids against formaldehyde-induced nephropathy in rats," *Toxicol Ind Health* 2006; 22: 223-9; Ellulu M S, Khaza'ai H, Patimah I et al. "Effect of long chain omega-3 polyunsaturated fatty acids on inflammation and metabolic markers in hypertensive and/or diabetic obese adults: a randomized controlled trial," *Food Nutr Res* 2016; 60: 29268; Uygur R, Aktas C, Tulubas F et al. "Cardioprotective effects of fish omega-3 fatty acids on doxorubicin-induced cardiotoxicity in rats," *Hum Exp Toxicol* 2014; 33: 435-45, each incorporated herein by reference in its entirety.

In addition to natural products, several carrier systems have been developed to increase efficacy of cancer treatment and decrease toxicity such as liposomes. Liposomes consist of one or more lipid bilayers surrounding an aqueous core. They are a relatively safe delivery system because they are biocompatible and biodegradable. See Alhariri M, Azghani A, Omri A. "Liposomal antibiotics for the treatment of infectious diseases," *Expert Opin Drug Deliv* 2013; 10: 1515-32, included herein by reference in its entirety.

In view of the forgoing, one objective of the present invention is to provide a liposomal formulation that has beta-glucan, doxorubicin, and omega-3, -6, and/or -9 lipids, for an improved therapeutic liposome for cancer treatment.

BRIEF SUMMARY OF THE INVENTION

According to a first aspect, a therapeutic liposome having a bilayer enclosing an internal compartment, wherein the bilayer comprises at least one poly-unsaturated fatty acid selected from the group consisting of omega-3 fatty acid, omega-6 fatty, and omega-9 fatty acid, a beta-glucan, a cholesterol, and a doxorubicin that is encapsulated within the internal compartment. The beta-glucan and the doxorubicin is encapsulated in the liposome and the cholesterol is integral to the bilayer. The liposome has a diameter of 100 nm to 1.5 μm.

In some embodiments, the bilayer comprises a phospholipid having at least one fatty acid chain of carbon chain length $C_{12}$ to $C_{24}$.

In some embodiments, the phospholipid comprises a head group selected from the group consisting of a choline, an ethanolamine, a serine, an inositol, a PEG molecule, a cell-penetrating peptide, or an antibody.

In some embodiments, the phospholipid has the PEG head group, the PEG head group is PEG 3500 up to PEG 6000.

In some embodiments, the phospholipid comprises at least one poly-unsaturated fatty acid selected from the group consisting of omega-3 fatty acid, omega-6 fatty acid, and omega-9 fatty acid.

In some embodiments, the bilayer comprises a pH sensitive lipid.

In some embodiments, the beta-glucan is a linear or a branched (1,3) beta glucan, or a linear or a branched (1,3)(1,4)beta-glucan, or a combination thereof.

In some embodiments, the beta-glucan is derived from at least one organism selected from the group consisting of *Euglena gracilis*, bacteria, a mushroom fungus, a yeast, and a cereal source.

In some embodiments, the therapeutic liposome further has a second active agent selected from the group consisting of epirubicin, daunorubicin, idarubicin, valrubicin, or mitoxantrone and the second active agent is encapsulated within the internal compartment.

In some embodiments, the omega-3 fatty acid is selected from the group consisting of all-cis 7,10,13-hexadecatrienoic acid, all-cis-9,12,15-octadecatrienoic acid, all-cis-11,14,17-eicosatrienoic acid, all-cis-8,11,14,17-eicosatrienoic acid, all-cis-8,11,14,17-eicosatetraenoic acid, all-cis-5,8,11,14,17-eicosapentaenoic acid, all-cis-6,9,12,15,18-heneicosapentaenoic acid, all-cis-7,10,13,16,19-docosapentaenoic acid, all-cis-4,7,10,13,16,19-docosahexaenoic acid, all-cis-9,12,15,18,21-tetracosapentaenoic acid, and all-cis-6,9,12,15,18,21-tetracosahexaenoic acid.

In some embodiments, the omega-6 fatty acid is selected from the group consisting of all-cis-9,12-octadecadienoic acid, all-cis-6,9,12-octadecatrienoic acid, all-cis-11,14-eicosadienoic acid, all-cis-8,11,14-eicosatrienoic acid, all-cis-5,8,11,14-eicosatetraenoic acid, all-cis-13,16-docosadienoic acid, all-cis-7,10,13,16-docosatetraenoic acid, all-cis-4,7,10,13,16-docosapentaenoic acid, all-cis-9,12,15,18-tetracosatetraenoic acid, and all-cis-6,9,12,15,18-tetracosapentaenoic acid.

In some embodiments, the omega-9 fatty acid is selected from the group consisting of oleic acid, eicosenoic acid, mead acid, erucic acid, nervonic acid.

According to a second aspect, a method of treating a cancer in a subject, the method including administering a dose of a therapeutic liposome, wherein the dose is 0.1 mg/m²-100 mg/m² and the therapeutic liposome includes a bilayer comprising at least one poly-unsaturated fatty acid selected from the group consisting of omega-3 fatty acid, omega-6 fatty acid, and omega-9 fatty acid, a phospholipid having at least one fatty acid chain of carbon chain length $C_{12}$ to $C_{24}$, a beta-glucan, and a cholesterol, wherein the cholesterol is integral to the bilayer; and a doxorubicin, wherein the doxorubicin is encapsulated in the liposome. The liposome has a diameter of 100 nm to 1.5 µm. The phospholipid has a head group selected from the group consisting of a choline, an ethanolamine, a serine, an inositol, a PEG molecule, a cell-penetrating peptide, or an antibody, and a tail group of the phospholipid has at least one poly-unsaturated fatty acid. The beta-glucan is encapsulated in the liposome, and is derived from at least one organism selected from the group consisting of *Euglena gracilis*, bacteria, a mushroom fungus, a yeast, and a cereal source.

In some implementations of the method, the therapeutic liposome further includes a second active agent selected from the group consisting of epirubicin, daunorubicin, idarubicin, valrubicin, or mitoxantrone and the second active agent is encapsulated within the internal compartment.

In some implementations of the method, the beta-glucan is a linear or a branched (1,3) beta glucan, or a linear or a branched (1,3)(1,4)beta-glucan, or a combination thereof.

In some implementations of the method, the dose is repeated every 10-30 days when the cancer in the subject is not showing progression.

In some implementations of the method, the dose is delivered at a rate of 0.2 mg/min-2 mg/min.

In some implementations of the method, a cumulative dose does not exceed 400-600 mg/m².

In some implementations of the method, the cancer is at least one selected from the group consisting of an ovarian cancer, a multiple myeloma, a sarcoma, a colorectal cancer and a breast cancer.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
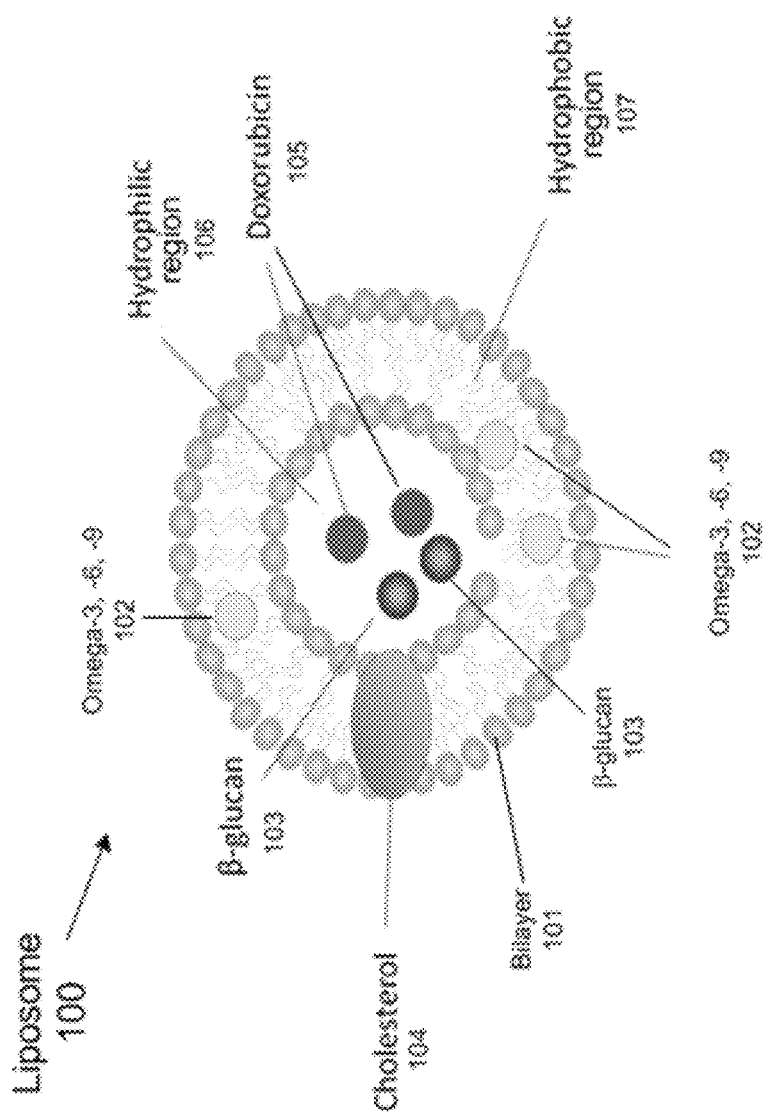
FIG. 1 is a schematic of an exemplary therapeutic liposome.

Throughout the specification ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Referring now to the drawings, wherein like reference numerals designate identical or corresponding parts throughout the several views.

According to a first aspect, a therapeutic liposome having a bilayer enclosing an internal compartment where the bilayer comprises at least one poly-unsaturated fatty acid selected from the group consisting of omega-3 fatty acid, omega-6 fatty acid, and omega-9 fatty acid, a beta-glucan, a cholesterol, and a doxorubicin. The beta-glucan and the doxorubicin are encapsulated in internal compartment of the liposome and the cholesterol is integral to the bilayer. FIG. 1 depicts an exemplary model of the therapeutic liposome 100, which includes the bilayer 101, the omega-3, -6, or -9 fatty acid 102, the β(beta)-glucan 103, the cholesterol 104, and the doxorubicin 105. FIG. 1 further depicts the hydrophilic region 106 of the liposome 100 and the hydrophobic region 107 of the liposome.

Throughout the specification a fatty acid may optionally be a fatty ester.

The therapeutic liposome of the present disclosure may have a diameter of 100 nm-1.5 µm, 500 nm-1.25 µm, or 750 nm-1 µm. To alter the diameter and a size of the liposome and minimize the dispersity of the size distributions, procedures such as freeze-thaw, sonication, extrusion, and high-pressure homogenization may be required. For example, an extrusion method may be used to prepare liposomes with controlled sizes determined by the pore size of a track-etched polycarbonate membrane.

In some embodiments, the bilayer 101 further comprises a phospholipid having at least one fatty acid chain of carbon chain length $C_{12}$ to $C_{24}$. A fatty acid is a carboxylic acid functional group on the $C_1$ of an aliphatic chain. Generally, phospholipids have a head group that is hydrophilic (i.e. phosphate) and two tail groups, of which one may be a fatty acid chain, which are hydrophobic and connected to a glycerol molecule by an ester bond via the carboxylic acid of the fatty acid chains. In the bilayer the phospholipid's tail groups face one another and the head groups are opposed. The therapeutic liposome of the present disclosure includes fatty acids having an aliphatic chain of $C_{12}$ to $C_{24}$, $C_{14}$ to $C_{22}$, or $C_{16}$ to $C_{20}$. Exemplary fatty acids may include, but are not limited to lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid. Hereafter, when referring to fatty acids connected, attached, or bound to a glycerol, or a phospholipid, the fatty acid is in reacted form as an ester.

The phospholipid head group generally includes a phosphate, but the phosphate may provide a linker between the glycerol and another head group molecule in order to attain different properties of the phospholipid, or as in the case of the therapeutic liposome of the present disclosure, to improve targeting to cancer tumors or in vivo retention without rejection or immune response activation. In some embodiments, the phospholipid comprises a head group selected from the group consisting of a choline, an ethanolamine, a serine, an inositol, a PEG molecule, a cell-penetrating peptide (CPP), or an antibody. Choline, ethanolamine, serine, and inositol are naturally occurring in nature and may be included in the therapeutic liposome attached via phosphoester bonds. The percentage by weight of phospholipid relative to the total lipid weight of the bilayer is 20%-90%, about 40%-80%, or about 50%-70%.

Natural phospholipids may be obtained from various sources such as soya bean or egg yolk. In terms of the polar headgroups, phospholipids are classified as phosphatidylcholine (PC), phosphatidylethanolamine (PE), phosphatidylserine (PS), phosphatidylinositol (PT), phosphatidylglycerol (PG) and phosphatidic acid (PA). PC and PE are the most abundant phospholipids in plants and animals and are also the most used to produce liposomes. However, natural phospholipids are less stable than the synthetic phospholipids. Synthetic phospholipids may be produced from natural lipids. The modification of the non-polar and polar regions of phospholipid molecules allows the creation of an unlimited variety of well-defined and characterized phospholipids. Examples of synthetic lipids include, but are not limited to dipalmitoyl phosphatidylcholine (DPPC), dimyristoyl phosphatidylcholine (DMPC), distearoyl phosphatidylcholine (DSPC) and hydrogenated soy phosphatidylcholine (HSPC), 1-palmitoyl-2-oleoyl-sn-glycero-3-phosphocholine (POPC), (1-palmitoyl-2-stearoyl(5-DOXYL)-sn-glycero-3phosphocholine (SLPC), 1,2-dioleoyl-sn-glycero-3-phosphocholine (DOPC), 1,2-distearoyl-sn-glycero-3-phospho-(1'-rac-glycerol) (DSPG), 1,2-dipalmitoyl-sn-glycero-3-phosphoglycerol (DPPG) and 1,2-distearoyl-sn-glycero-3-phosphate (DSPA). Unnatural lipids may be included as well in which choline, ethanolamine, serine, and inositol are not linked to the glycerol via the phosphate group, but directly to glycerol or via an hydroxy acid. To form an ether linkage between a hydroxyl group in glycerol or the hydroxyl end of the hydroxy acid, and either choline or ethanolamine, may be completed by a bimolecular dehydration of the alcohol groups by adding a strong acid (e.g. sulfuric acid) to a glyerolipid with one available hydroxyl group on the glycerol and heating to a temperature of 120° C.-150° C. Other methods may include a Williamson ether synthesis requiring a tosylated choline or ethanolamine or halogenation of choline or ethanolamine. The hydroxy acid may be an alpha hydroxy acid, a beta hydroxy acid, a gamma hydroxy acid or an omega hydroxy acid. Exemplary hydroxy acids may include, but are not limited to 2-hydroxy propanoic acid, 3-hydroxy propanoic acid, 2-hydroxy butanoic acid, 3-hydroxy butanoic acid, 4-hydroxy butanoic acid, 2-hydroxy pentanoic acid, 3-hydroxy pentanoic acid, 4-hydroxy pentanoic acid, 16-hydroxy palmitic acid, and 18-hydroxy stearic acid.

PEG, CPP and antibodies may be synthetically attached to lipids having a phosphate head group or the phosphate head group may be replaced by the hydroxy acid, as described herein, or only the glycerolipid without a headgroup. PEG may be attached to a glycerolipid via an ether linkage formed by the bimolecular dehydration as described herein, peptides may be attached to a glycerolipid via an ester bond or via an amine by nucleophilic substitution methods know to those in the art.

PEG is a polyether compound with applications in medicine. PEG may be categorized by its molecular weight and structure. PEG may be linear, branched, star, or comb shapes. PEG may categorized by the average molecular weight up to 20,000 g/mol. In nomenclature of PEG the number that follows the word "PEG" refers to the average molecular weight of PEG in the mixture. In some embodiments of the therapeutic liposome of the present disclosure, the PEG attached to a glycerolipid or phospholipid is PEG 3500 up to PEG 6000, PEG 4000 to PEG 5000, or PEG 4250 to PEG 4750. PEG is further known to shield macromolecules from inactivation by the immune system and to de-target them from organs where they may build up and have a toxic effect when administered in vivo. PEGylated-lipids may be a percentage by weight relative to the total lipid bilayer of, but not limited to 5%-60%, about 10%-50%, or about 20%-40%.

CPPs are short peptides that facilitate cellular intake/uptake of various macromolecules, from nanosize particles to small molecules and large fragments of DNA in in vivo delivery. Exemplary CPPs may be peptides that decorate certain viral particles to assist viral particles gaining entry into cells. Such peptides include TAT, which is a partial viral peptide sequence, Pep-1, MPG, and polyarginine. The peptides may be either L- or D-isomers, but D-isomers are preferred so that enzymes cannot deteriorate the peptide in vivo. CPP attached lipids may be a percentage by weight relative to the total lipid bilayer of, but not limited to 5%-60%, about 10%-50%, or about 20%-40%.

As used herein "antibody" or "antibodies" may include a full antibody including the heavy and light chains or only portions of the full antibody such as only a heavy chain, only a light chain, or only the functional antigen-binding (Fab) domains. Antibodies may be attached to a phospholipid, a glycerolipid, or a glycerolipid with the hydroxy acid linker, by an avidin-biotin complex. Biotin may be attached to the glycerolipid (with or without the hydroxy acid linker) or phospholipid via an ester bond or a phosphoester bond with biotin, and avidin may label the antibody for the organ of interest. The avidin-biotin complex is the strongest known non-covalent interaction ($K_d=10^{-15}$ M) between a protein and ligand. The bond formation between biotin and avidin is very rapid, and once formed, is unaffected by extremes of pH, temperature, organic solvents and other denaturing agents. Avidin may further be monovalent (i.e. binding site for one biotin molecule) or divalent (i.e. two binding sites for one biotin molecule each) for the present application, however avidin may have up to tetravalency. Relevant to the present disclosure, for example, a divalent avidin may be attached to an anti-tumor antibody via a biotin on the anti-tumor antibody, purified, and then mixed with a glycolipids and/or phospholipids having a biotin attached as described herein. The glycerolipids or phospholipids may be in the bilayer or individual biotin-labeled glycerolipids (with or without the hydroxy acid linked) or biotin-labeled phospholipids by methods well-known in the art to attach to the antibody. Other mechanisms of attaching antibodies to lipids include thiolation of antibodies with 3-(2-pyridyldithio) propionic acid-N-hydroxysuccinimide ester (SPDP), followed by deprotection with dithiothreitol (DTT) and conjugation to liposomes containing maleimide-derivatized lipids. Additional methods familiar in the art may be used as well. See Antibody Conjugation Methods for Active Targeting of Liposomes, Chapter 4 of "Methods in Molecular medicine. Vol. 25: Drug Targeting: Strategies, Principles, and Applications," Edited by G. E. Francis and C. Delgado© Humana Press Inc. Totawa, N.J., incorporated by reference herein in its entirety. Antibody attached lipids may be a percentage by weight relative to the total lipid bilayer of, but not limited to about 25%-75%, about 30%-60%, or about 40%-50%.

Hereafter, "glycerolipid" may refer to both the hydroxy acid modified glycerolipid and the unmodified glycerolipid. Further, in some embodiments, the phospholipid or glycerolipid comprises at least one poly-unsaturated fatty acid selected from the group consisting of omega-3 fatty acid, omega-6 fatty acid, and omega-9 fatty acid. Poly-unsaturated fatty acids are fatty acids that contain more than one double bond in their backbone. This class includes many important compounds, such as essential fatty acids. Omega-3 and omega-6 fatty acids have two or more cis double bonds that are separated from each other by a single methylene bridge ($-CH_2-$ unit). For example, of the two lipid chains attached to the first and second hydroxyl group of the glycerol molecule that makes up the glycerolipid or phospholipid, one may be palmitate and one may be an omega-3 fatty acid, an omega-6 fatty acid, or an omega-9 fatty acid.

In some embodiments, the poly unsaturated fatty acid may be integral to the bilayer as a free fatty acid, not attached to a glycerolipid or phospholipid structure.

In some embodiments of the liposome, the lipids in the bilayer may comprise polyunsaturated fatty acids at a percentage by weight relative to the total lipid content of about 1%-40%, about 5%-35%, about 10%-25%, or about 15%-20%.

In some embodiments of the liposome, the polyunsaturated fatty acids may be in a molar ratio with the phospholipids of 0.1:4-1:1 or 0.5:3-1:2.

In some embodiments, the omega-3 fatty acid may be, but is not limited to all-cis 7,10,13-hexadecatrienoic acid, all-cis-9,12,15-octadecatrienoic acid, all-cis-11,14,17-eicosatrienoic acid, all-cis-8,11,14,17-eicosatrienoic acid, all-cis-8,11,14,17-eicosatetraenoic acid, all-cis-5,8,11,14,17-eicosapentaenoic acid, all-cis-6,9,12,15,18-heneicosapentaenoic acid, all-cis-7,10,13,16,19-docosapentaenoic acid, all-cis-4,7,10,13,16,19-docosahexaenoic acid, all-cis-9,12,15,18,21-tetracosapentaenoic acid, and all-cis-6,9,12,15,18,21-tetracosahexaenoic acid. In some embodiments, the omega-6 fatty acid may be, but is not limited to all-cis-9,12-octadecadienoic acid, all-cis-6,9,12-octadecatrienoic acid, all-cis-11,14-eicosadienoic acid, all-cis-8,11,14-eicosatrienoic acid, all-cis-5,8,11,14-eicosatetraenoic acid, all-cis-13,16-docosadienoic acid, all-cis-7,10,13,16-docosatetraenoic acid, all-cis-4,7,10,13,16-docosapentaenoic acid, all-cis-9,12,15,18-tetracosatetraenoic acid, and all-cis-6,9,12,15,18-tetracosapentaenoic acid. In some embodiments, the omega-9 fatty acid may be, but is not limited to oleic acid, eicosenoic acid, mead acid, erucic acid, nervonic acid.

The therapeutic liposome of the present disclosure is configured to deliver doxorubicin to the cancer tumor in the subject. Once the liposome is in proximity of the tumor, the liposome may be internalized by a tumor cell at a surface of a tumor. The internalization process by the tumor is often via an endocytic vesicle. The endocytic vesicle of animal cells may undergo extensive changes including pH, recruitment of digestive enzymes and ion influx or efflux. Enzymes may be activated by pH changes or changes in ion concentration within the endocytic vesicle. To release the doxorubicin into the tumor, may necessitate dissipating the liposome, therefore, in some embodiments, the bilayer comprises a pH sensitive lipid. The pH sensitive lipid may be, but is not limited to N-palmitoyl homocysteine, 1,2-dioleoyl-sn-glycero-3-succinate, 1,2-dipalmitoyl-sn-glycero-3-succinate, and N-(4-carboxybenzyl)-N,N-dimethyl-2,3-bis(oleoyloxy)propan-1-aminium. The therapeutic liposome may comprise a percentage by weight of the pH sensitive lipid relative to the total lipid bilayer composition of, but not limited to about 0%-50%, about 5%-40%, about 10%-30%, or about 15%-20%. DOX included in the therapeutic liposome is stable at physiological low pH (pH 3-5) and pH inside endosomes and lysosomes may be from pH 3-7.2.

The therapeutic liposome of the present disclosure includes beta-glucan. In some embodiments, the beta-glucan is derived from at least one organism selected from the group consisting of *Euglena gracilis*, bacteria, a mushroom fungus, a yeast, and a cereal source. The beta-glucan may be derived from a variety of natural sources including, but not limited to *Euglena*, a protist, bacteria, such as gram-positive or gram negative bacteria including *Escherichia, Streptococcus, Salmonella, Serratia, Shigella, Pseudomonas, Neisseria, Haemophilus, Agrobacterium,* or *Rhizobium*; a mushroom fungus, such as Chinese Reishi (*Ganoderma lucidum*), or Japanese Shiitake (*Lentinula edodes*) and Maitake (*Grifola frondosa*), arboreal fungi: Chaga (*Inonotus obliquus*), Turkey Tail (*Trametes versicolor*), Split Gill (*Schizophyllum commune*), Mulberry Yellow Polypore (*Phellinus linteus*) and cultivated fungi, Hiratake (*Pleurotus ostreatus*, Oyster mushroom); a yeast, such as *Schizosaccharomyces pombe, Saccharomyces cerevisiae,* or *Saccharomyces pastorianus*; and/or a cereal source, such as oat, barley, wheat, rye, sorghum, or rice.

The beta-glucans included in the therapeutic liposome may include, curdlan, laminaran, pachymaran, lentinan, pleuran, schizophyllan, sclerotinan, sclero-beta-glucan, grifolan, yeast beta-glucan, or barley beta-glucan. Beta-glucans derived from different sources vary in molecular weight. The beta-glucans included in the therapeutic liposome may have a molecular weight about 10 kDa to about 500 kDa, about 20 kDa to about 450 kDa, about 50 kDa to about 400 kDa, about 75 kDa to about 350 kDa, about 100 kDa to about 300 kDa, about 125 kDa to about 275 kDa, about 150 kDa to about 250 kDa, or about 175 kDa to about 225 kDa.

In some embodiments of the therapeutic liposome, the beta-glucan is synthetically prepared. Beta-glucans may be synthetically prepared by methods including solid phase synthesis or solution phase synthesis. The methods may include beta-glucan derived from the natural sources as described herein, and synthetically combined with beta-glucans prepared by solid phase or solution phase synthesis methods. The beta-glucan may be obtained from commercial products such as Drago-Beta Glucan, SymGlucan®, or the like.

In some embodiments, the beta-glucan is a linear or a branched (1,3) beta glucan, or a linear or a branched (1,3)(1,4)beta-glucan, or a combination thereof. Beta-glucans incorporated in some embodiments of the therapeutic liposome may have a degree of branching in weight percentage of about 0.1% to about 99% branched, about 0.5% to about 90% branched, about 1% to about 85% branched, about 1.5% to about 80% branched, about 2% to about 70% branched, about 2.5% to about 6% branched, about 3% to about 50% branched, about 3.5% to about 40% branched, about 4% to about 30% branched, about 4.5% to about 20% branched, about 5% to about 18% branched, about 6% to about 16% branched, about 7% to about 14% branched, about 8% to about 12% branched, about 9% to about 10% branched, relative to the total beta-glucan content. In the therapeutic liposome the weight percentage of (1,3) beta glucan relative to (1,3)(1,4)beta-glucan may be in the range of, but not limited to about 0%-95%, about 10%-80%, about 20%-70%, about 30%-60%, or about 40%-50%.

Some beta-glucans are water insoluble, but in some embodiments of the therapeutic liposome, the beta-glucan is sulfonated, phosphorylated, aminated, and/or nitration. For example, beta-glucans may be sulfonated by chlorosulfonic acid addition to a solution of beta-glucan. For example, phosphorylation of beta-glucan may be achieved by mechanochemical phosphorylation methods employing a planetary ball mill. For example, amination of beta-glucan may be accomplished by oxidizing an hydroxyl of a terminal glucose of the beta-glucan to an aldehyde by an oxidizing agent such as sodium periodate, then adding sodium triacetoxyborohydride to reduce the aldehyde to an amine. For example, nitration of beta-glucans may be achieved by adding nitric acid and sulfuric acid to a solution of beta-glucan. Beta-glucan may be best solubilized in a polar aprotic solvent such as dimethyl sulfoxide, acetonitrile, or other polar-aprotic solvents known in the art.

In some embodiments, the therapeutic liposome may include the beta-glucan in an amount of, but not limited to about 10 μg/mL to 40 μg/mL, about 15 μg/mL to 35 μg/mL, about 20 μg/mL to 30 μg/mL, or about 22 μg/mL to 28 μg/mL.

The therapeutic liposome of the present disclosure further includes cholesterol. Cholesterol is a class of compounds called sterols (a modified steroid). Sterols are a lipid molecule and are biosynthesized by all animal cells because it is an essential structural component of all animal cell membranes that is required to maintain both membrane structural integrity and fluidity. Cholesterol may enable animal cells to protect membrane integrity and cell viability thus allowing animal cells to change shape and animal cells to move (unlike bacteria and plant cells which are restricted by their cell walls). The hydroxy group on cholesterol may interact with the polar head groups of the membrane lipids, while the bulky steroid and the hydrocarbon chain are embedded in the membrane, alongside the nonpolar fatty-acid chain of the other lipids. Through the interaction with the phospholipid and/or glycerolipid fatty-acid chains, cholesterol increases membrane packing, which both alters membrane fluidity and maintains membrane integrity. Exemplary sterols may include, but are not limited to cholesterol, dihydrocholesterol, lanosterol, dihydrolanosterol, sitosterol, campesterol, stigmasterol, brassicasterol, ergosterol, phytosterol (the mixture thereof), and hydrogenated phytosterol. The preferred sterol for the therapeutic liposome is cholesterol and dihydrocholesterol. The therapeutic liposome may include a molar ratio of the total lipids to cholesterol in a range of, but not limited to about 7:1 to 2:3, about 4:1 to 4:5, or about 2:1 to 1:1.

In some embodiments, the therapeutic liposome further has a second active agent which may be an additional anthracycline, a class of drugs used in cancer chemotherapy derived from *Streptomyces* bacterium *Streptomyces peucetius* var. *caesius*. Exemplary anthracyclines include epirubicin, daunorubicin, idarubicin, valrubicin, and mitoxantrone. The second active agent included in the therapeutic liposome may be in an amount of 2 μg/mL to 50 μg/mL, about 15 μg/mL to 45 μg/mL, about 20 μg/mL to 40 μg/mL, about 25 μg/mL to 35 μg/mL or about 28 μg/mL to 30 μg/mL. In some embodiments, the therapeutic liposome may further include other classes of cancer chemotherapy agents including signal transduction inhibitors (Gefitinib, CI-1033, EKB-569, PKI-166, and the like), gene expression modulators (synthetic polyamides, RNAi molecules, trichostatin A, and the like), and/or angiogenesis inhibitors (VEGFR-1, Angiopoietin 2, TSP-1, angiostatin, endostatin, and the like). Other classes of cancer chemotherapy agents may be included in the therapeutic liposome at a concentration of, but not limited to 0.5 μg/mL-50 μg/mL, 1 μg/mL-40 μg/mL, 10 μg/mL-30 μg/mL, 20 μg/mL-25 μg/mL.

The doxorubicin included in the therapeutic liposome may take many forms. Several thousands of DOX derivatives exist which may be included in the therapeutic liposome of the present disclosure. An exemplary list of DOX derivatives includes, but is not limited to amino derivatives of doxorubicin, morpholino derivatives of doxorubicin (e.g. 3'-morpholino-doxorubicin), nitro-derivatives of doxorubicin, benzyl-derivatives of doxorubicin, alkoxy-derivatives of doxorubicin, or aminoglycoside- and glycoside-derivatives of doxorubicin. DOX derivatives may be specifically modified on the C-9 and/or C-10 carbons of the anthracycline structure of DOX. Further, DOX derivatives modified at the C-14 carbon may be included. The doxorubicin-derivatives included in the liposome relative to DOX may be, but not limited to about 0%-80%, about 5%-70%, about 10%-60%, about 20%-50%, or about 30%-40%. In some embodiments, the therapeutic liposome may include a doxorubicin derivative that is in pro-drug form which becomes an active drug upon hydrolysis at low pH inside an endosome or lysosome of a cell which has endocytosed a liposome containing the pro-drug DOX. Upon the pH lowering in the endosome or lysosome, which may break up the liposome and release the dox upon the lowering of the pH, as may happen inside an endosome or lysosome.

In some embodiments, the cholesterol and the beta-glucan may be covalently linked, such that the cholesterol is configured to anchor in the membrane, while the beta-glucan is in the hydrophilic region 106 inside of the liposome 100. Exemplary linkers may include, but are not limited to an amino acid, a polypeptide linker, an acid labile linker, a hydroxy acid linker as described herein, methoxy-PEG 200-PEG 400, or via modification of the beta-glucan by a carboxymethyl group.

In some embodiments, the cholesterol, the beta-glucan, and the doxorubicin, or a combination thereof is covalently linked. The cholesterol, the beta-glucan, and the doxorubicin, or a combination thereof may be covalently linked by an acid labile linker. For example, the doxorubicin has hydroxyl groups which may be used as attachment points. An exemplary acid labile linker may be 6-(2,5-dioxo-2,5-dihydro-1H-pyrrol-1-yl)-N-(4-(((2,5-dioxo-2,5-dihydro-furan-3-1)methyl)thio)phenyl)hexanamide, poly(β-1-malic acid), or other linkers as described in the thesis of Kevin Maier (2012) "Design of an Acid Labile Traceless-cleavable Click Linker for Use in a Novel Protein Transduction Shuttle," Ludwig-Maximilians-Universität München, or Patent publication EP0495263B1.

According to a second aspect, a method of treating a cancer in a subject, the method includes administering a dose of the therapeutic liposome, as described herein, wherein the dose is, but not limited to about 0.1 mg/m$^2$-100 mg/m$^2$, about 1 mg/m$^2$-90 mg/m$^2$, about 5 mg/m$^2$-75 mg/m$^2$, about 10 mg/m$^2$-60 mg/m$^2$, about 20 mg/m$^2$-50 mg/m$^2$, or about 30 mg/m$^2$-40 mg/m$^2$. The therapeutic liposome may be delivered by IV perfusion to a patient having a variety of cancers that may include, but are not limited to ovarian cancer, a multiple myeloma, a sarcoma, a colorectal cancer, and a breast cancer.

In some implementations of the method, the dose is repeated every 10-30 days, 15-25 days, or 20-22 days when the cancer in the subject is not showing progression. Progression may be indicated by a reduction in the size of the tumor, reduction in the swelling of lymphnodes proximal to the tumor, or blood based markers, known in the art, return to levels of a subject not presently presenting with cancer of any type.

In some implementations of the method, the dose is delivered at a rate of, but not limited to 0.2 mg/min-2 mg/min, 0.5 mg/min-1.5 mg/min, or 1 mg/min-1.25 mg/min.

The rate of the delivery of the dose may be regulated by the subjects blood filtering capability that is measured separately by a physician. The rate of delivery of the dose must be regulated to reduce uptake into the non-cancer organs such as spleen, liver and kidneys.

In some implementations of the method, a cumulative dose does not exceed 400-600 mg/m$^2$, 450-550 mg/m$^2$, or 475-525 mg/m$^2$. The cumulative dose must be monitored closely to prevent over dosage which may result in cardiotoxicity which may result in death.

Pharmaceutical compositions suitable for injectable use on the therapeutic liposome include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the therapeutic liposome must be sterile and should be fluid to the extent that easy syringability exists. The solutions for injection must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants that do not interfere with the liposome formation. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition.

The example below is intended to further illustrate an exemplary embodiment of the therapeutic liposome and is not intended to limit the scope of the claims.

EXAMPLE 1

Methodology
Liposomes Preparation

Liposomal formulation was prepared by dehydration-rehydration technique. 1,2-dipalmitoyl-sn-glycero-3-phosphocholine (DPPC), cholesterol and omega-3 in molar ratio of 3:0.5:1.5 were dissolved in chloroform:methanol (2:1 v/v). The organic solvent was then evaporated in rotary evaporator for 10 min at 45 C.°. The lipid film then was rehydrated with 100 μg/ml of doxorubicin and 0.5 mg of β-glucan. The suspension lipids were then sonicated for 30 min. Liposomes were extruded 11 times through 400 nm and then 100 nm polycarbonate filters. The extruded liposomes were divided to aliquot and frozen for 15 min at −70° C. and then freeze-dried overnight. Liposomal omega-3, liposomal β-glucan and liposomal doxorubicin were prepared to be used as control in further experiments. To rehydrate the powder formulation, sterile distilled water was added in the volume of 10% of the volume before lyophilisation, vortexed, and then incubated for 30 min at 45° C.; then PBS was added to form the original volume. The solution was centrifuged for 20 min, at 100,000×g and 4° C. and the supernatant was removed. This step was repeated by PBS. The size of liposomes was determined by a submicron particle sizer Malvern.

Encapsulation Efficiency

The entrapped β-glucan and doxorubicin that was released from the liposomes by 0.2% Triton X-100 (v/v, with PBS) was measured. β-glucan was determined using 1,3:1, 6-β-glucan (yeast/mushroom) assay kit (Megazyme, Ireland) according to manufacture protocol. For β-glucan detection, 0.1 ml of the supernatant was mixed 0.1 ml of reagent 1 of β-glucan kit and incubated for 1 hour at 40 C.°. Then, 3 ml of GOPOD reagent (bottle 4) of β-glucan kit was added and incubated for 20 min at 40 C.°. Absorption was measured at 510 nm and concentration of β-glucan was extracted from equation of β-glucan standard curve previously constructed. For doxorubicin, 0.5 ml was diluted 5 times and measured spectrophotometrically at 482 nm. Concentration was measured from a standard curve of different concentration of doxorubicin.

Table 1 shows the encapsulation efficiency of doxorubicin and beta-glucan based on the above methodology. Further the average size (diameter nm) of the liposome upon rehydration was determined by the above described methodology and listed in the table.

TABLE 1

Therapeutic liposome characteristics.

| | Encapsulation efficiency of beta-glucan (μg/ml) | Encapsulation efficiency of doxorubicin (μg/ml) | Size (nm) |
|---|---|---|---|
| Omelipdoxglu-3 | 35.2 ± 8.7 | 20.4 ± 3.1 | 905 ± 45 |

Cytotoxicity Assay
MTT Assay

Figure 2:
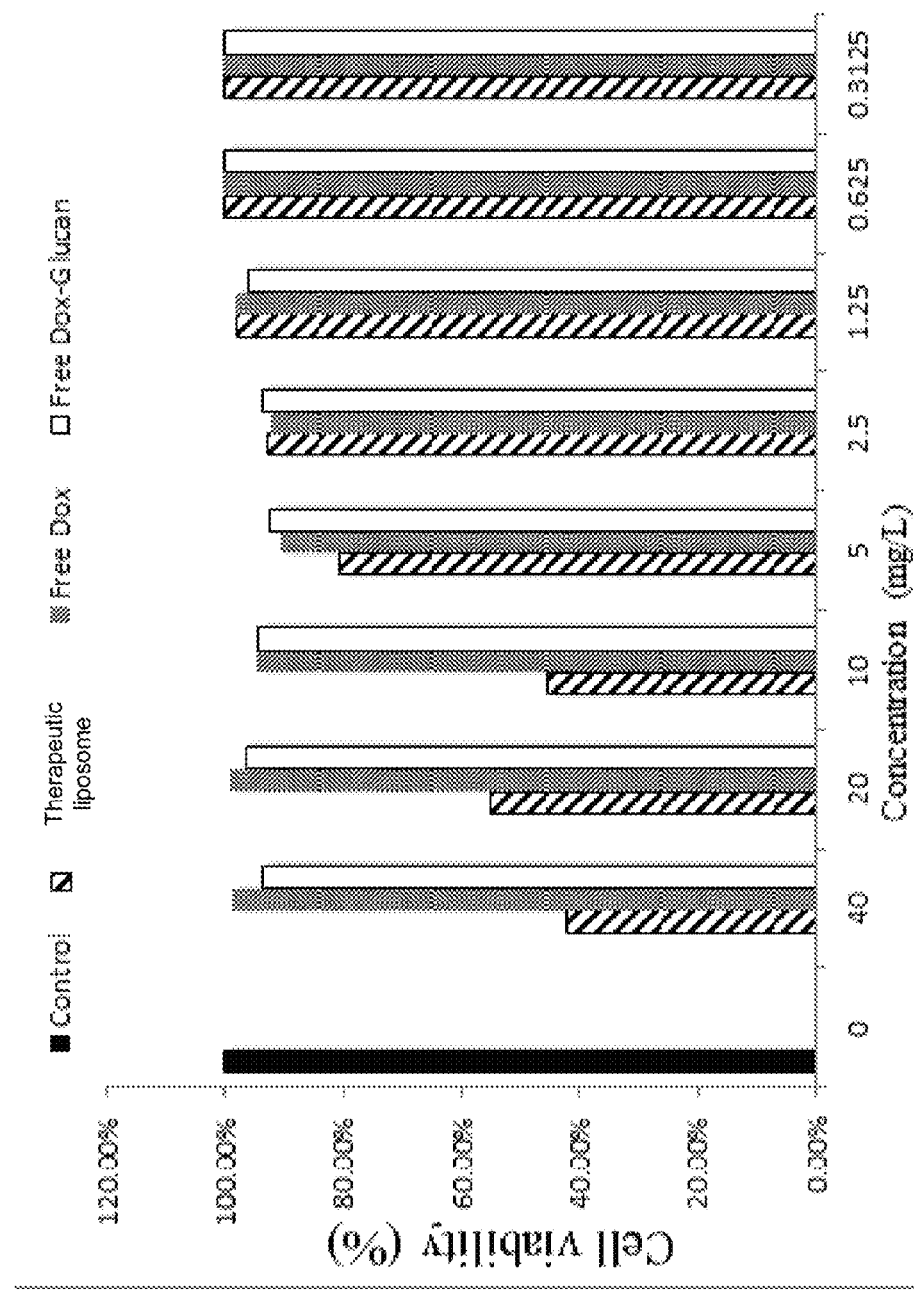
FIG. 2 is a graph of exemplary data on the cell viability of cells treated with the therapeutic liposome, free doxorubicin, and free doxorubicin and beta-glucan based on an MTT assay.
Figure 3:
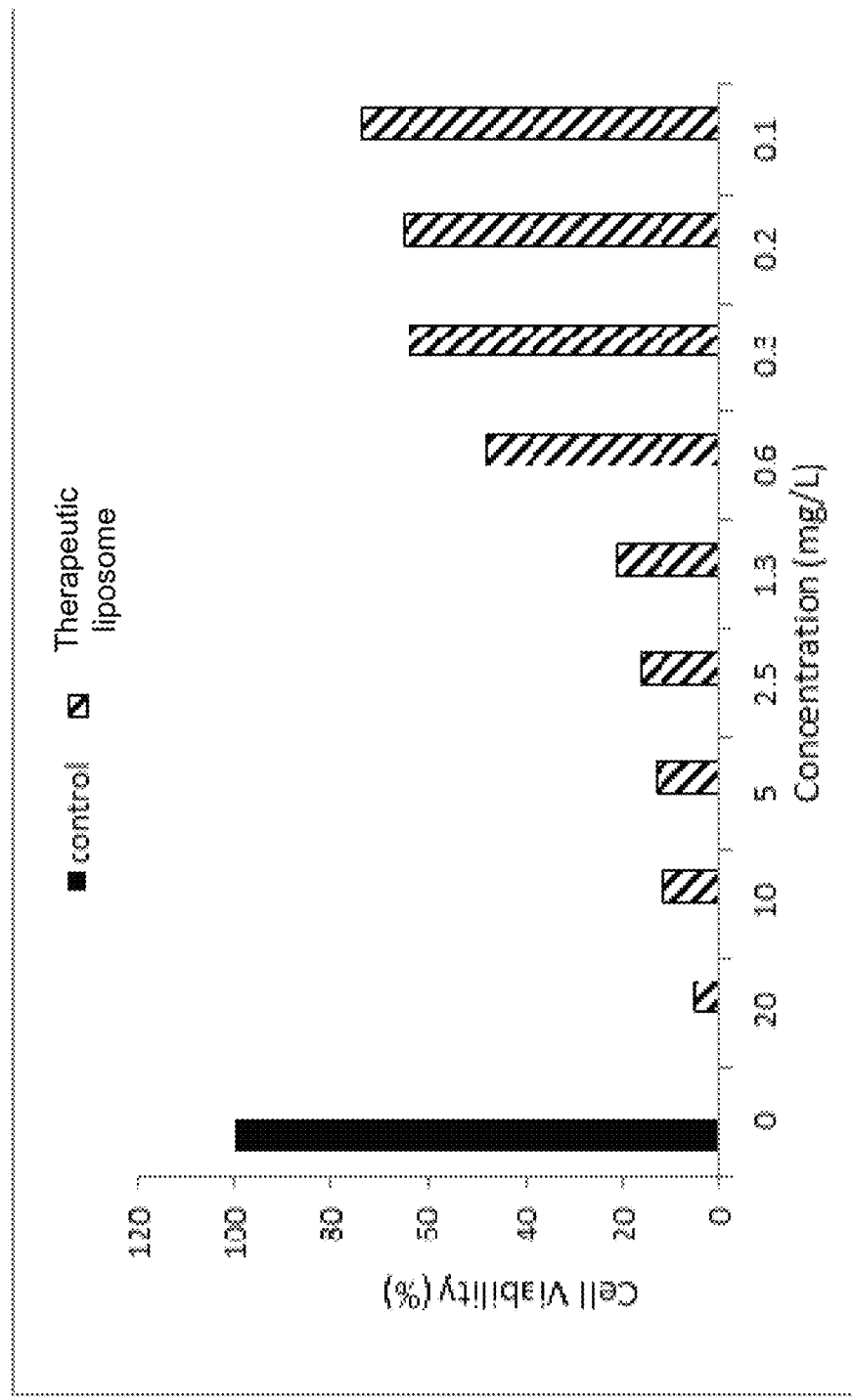
FIG. 3 is a graph of exemplary data on the cell viability of cells treated with the therapeutic liposome relative to a control at low concentrations based on an MTT assay.
Figure 4:
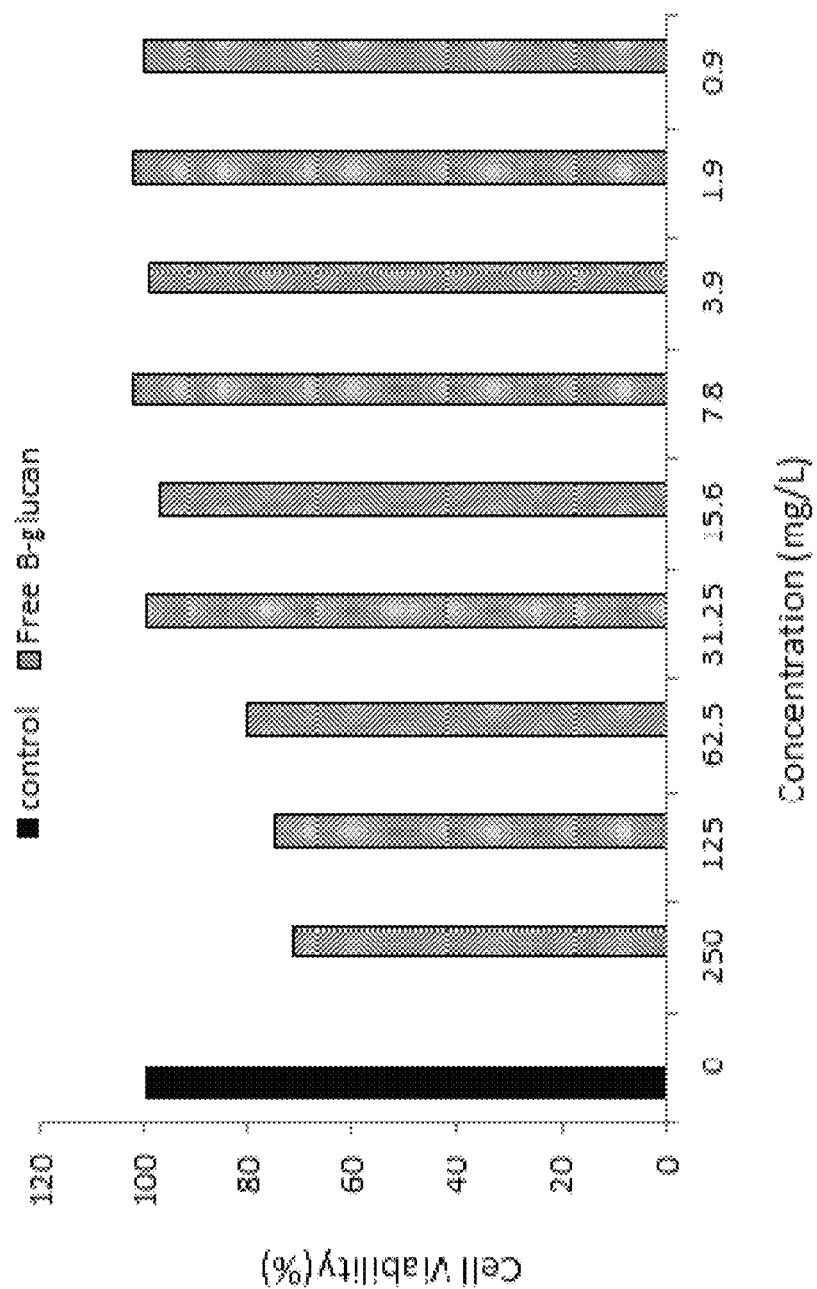
FIG. 4 is a graph of exemplary data on the cell viability of cells treated with the beta-glucan relative to a control at high concentrations based on an MTT assay.

The cytotoxicity of the β-glucan containing liposomes was evaluated using a colorimetric 3-(4,5-dimethylthiazol-2-yl)-2,5-diphenyltetrazolium bromide (MTT) assay. Carcinoma cell line was cultured in DMEM (Hyclone) supplemented with 10% FBS. Cells were maintained using standard cell culture procedures, through incubation in a humidified atmosphere at 37° C., 5% CO$_2$. Cells were passaged at sub-confluency, and all cells were used at late passage. At sub-confluency, the cells were seeded into 96-well plates at a density of 5×10$^3$ cells/well. In all instances, cells were allowed to adhere overnight, prior to treatment. Next, the cultures were incubated with 0.31, 0.62, 1.25, 2.5, 5, 10, 20 and 40 mg/L of liposomal β-glucan+doxorubcin for 24 h. The excess liposomes were removed by careful washing with PBS. Then, 200 μl of MTT solution (0.5 mg/ml in PBS) was added and the cells were incubated for another 4 h at 37° C. The reaction product was solubilized in 200 μl DMSO and absorbance (Abs) was measured at 570 nm. For all studies, negative controls included untreated cells (media alone) and media containing 50% D-PBS (HyClone) (this accommodated the maximum amount of PBS that may be released from the empty liposome formulations). H$_2$O$_2$ was chosen as a positive control, as it had been shown that H$_2$O$_2$ can induce apoptosis in the A549 cell line. The cell viability was calculated using the following formula: cell viability=(Absorbance of sample/Absorbance of negative control)×100. The viability of untreated controls was normalized to 100%. Cytotoxicity=100-% cell viability. FIG. 2, FIG. 3, and FIG. 4 depict the results of the MTT assay. FIG. 2 depicts a comparison of the therapeutic liposome with free doxorubicin and free doxorubicin and beta glucan in combination. The therapeutic liposome exceeded or met the same level of cell killing at all concentrations tested between 0.3125 mg/mL-40 mg/mL. However the cell killing at 5 mg/mL to 40 mg/mL of the therapeutic liposome exceeded the results of the tested compounds. FIG. 3 depicts the cell killing ability of very low concentrations (0.1 mg/mL-20 mg/mL) of the therapeutic liposome. FIG. 4 depicts the cell killing ability of free beta-glucan at higher concentrations (0.9 mg/mL-250 mg/mL). In a comparison across FIG. 3 and FIG. 4, the therapeutic liposome outperforms the free beta-glucan in cell killing ability as measured by cell viability from the MTT assay.

Figure 5:
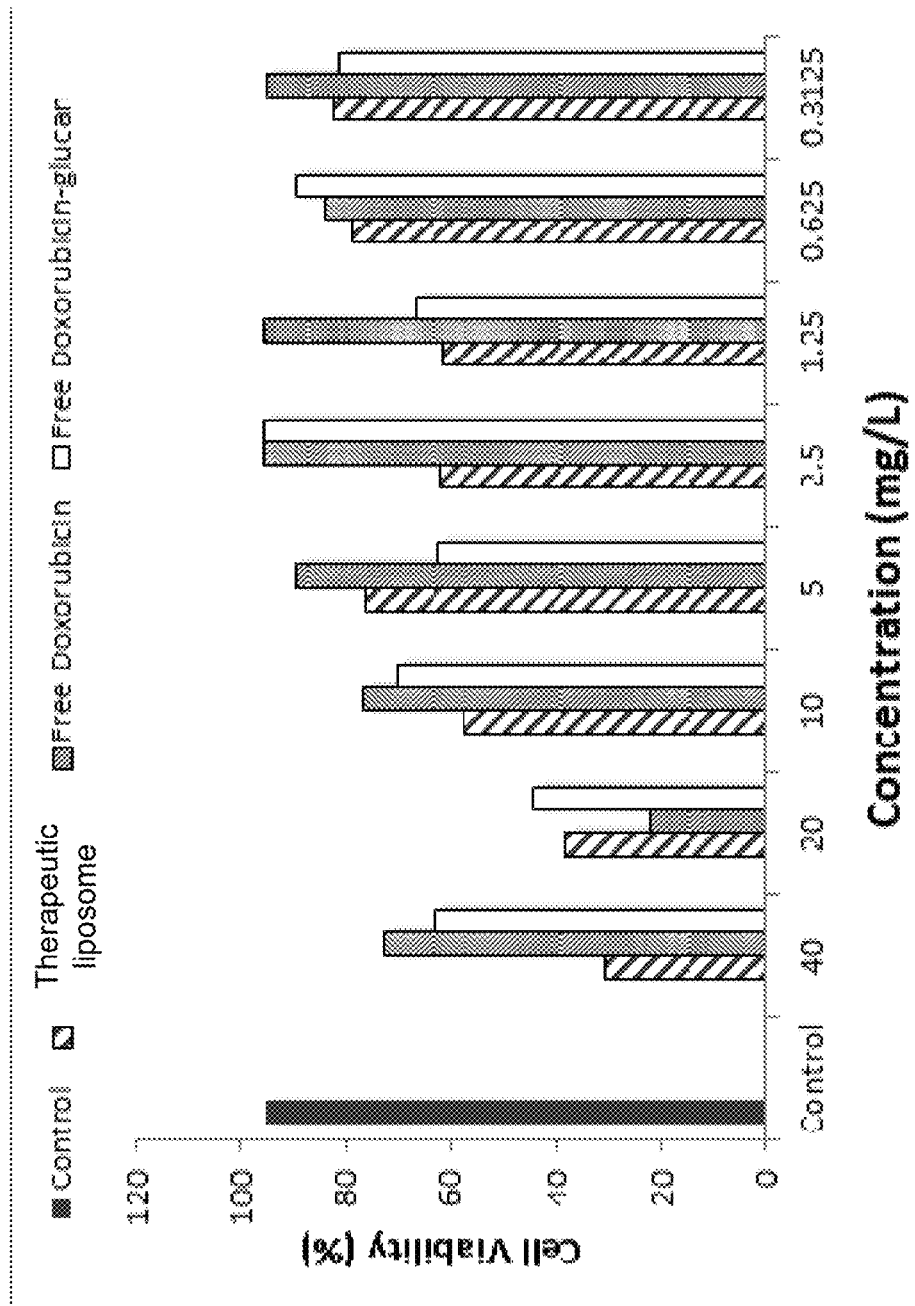
FIG. 5 is a graph of exemplary data on the cell viability of cells treated with the therapeutic liposome, free doxorubicin, and free doxorubicin and beta-glucan based on a trypan blue assay.

Trypan Blue Assay:

The cytotoxicity of the β-glucan containing liposomes was evaluated using a trypan blue assay. Carcinoma cell line was cultured in DMEM (Hyclone). Cells were maintained using standard cell culture procedures. Cells were incubated in a humidified atmosphere at 37° C., 5% $CO_2$. Cells were passaged at sub-confluency and all cells were used at late passage. Cell pellets were resuspended in 1 ml PBS. Next, the cultures were incubated with 0.31, 0.62, 1.25, 2.5, 5, 10 and 20 mg/L of liposomal β-glucan encapsulated doxorubicin for 24 h. The excess liposomes were removed by careful washing with PBS. Trypan blue was mixed at 1 part of 0.4% trypan blue and 1 part cell suspension (1:1 v/v). The mixture was incubated for 3 minutes at room temperature, then a drop of the trypan blue mixture was added to the haemocytometer. The percentage of viable cells ware calculated as follows: viable cells (%)=total number of viable cells per ml of aliquot/total number of cells per ml of aliquot×100. FIG. 5 depicts the cell viability under trypan blue tests. The therapeutic liposome met the same level of cell killing or exceeded the level of cell killing of free doxorubicin and beta-glucan in a combined mixture at each tested concentration between 0.3125 mg/mL and 40 mg/mL.

The invention claimed is:

1. A therapeutic liposome comprising:
   a bilayer enclosing an internal compartment, wherein the bilayer comprises:
      all-cis-9,12,15-octadecatrienoic acid; and
      a phospholipid having at least one fatty acid chain of carbon chain length $C_{12}$ to $C_{24}$, wherein the all-cis-9,12,15-octadecatrienoic acid is not attached to the phospholipid, and the phospholipid comprises a head group selected from the group consisting of a choline, an ethanolamine, a serine, an inositol, a PEG molecule, a cell-penetrating peptide, and an antibody in reacted form;
   a beta-glucan derived from oat, wherein the beta-glucan is encapsulated within the internal compartment;
   cholesterol, which is integral to the bilayer; and
   doxorubicin, which is encapsulated within the internal compartment;
   wherein the therapeutic liposome has a diameter in a range of 130 nm to 1.5 µm.

2. The therapeutic liposome of claim 1, wherein the phospholipid has the PEG molecule head group, and the PEG is PEG 3500 up to PEG 6000.

3. The therapeutic liposome of claim 1, wherein the phospholipid comprises at least one poly-unsaturated fatty acid selected from the group consisting of an omega-3 fatty acid, an omega-6 fatty acid, and an omega-9 fatty acid.

4. The therapeutic liposome of claim 1, wherein the bilayer further comprises a pH sensitive lipid.

5. The therapeutic liposome of claim 1, wherein the beta-glucan is a linear or a branched (1,3) beta glucan, or a linear or a branched (1,3)(1,4)beta-glucan, or a combination thereof.

6. The therapeutic liposome of claim 1, further comprising a second active agent which is an anthracycline selected from the group consisting of epirubicin, daunorubicin, idarubicin, valrubicin, and mitoxantrone, wherein the second active agent is encapsulated within the internal compartment.

7. A method of treating a cancer in a subject in need thereof, the method comprising:
   administering an effective amount of a therapeutic liposome to the subject, wherein the therapeutic liposome comprises:
      a bilayer enclosing an internal compartment, wherein the bilayer comprises:
         all-cis-9,12,15-octadecatrienoic acid; and
         a phospholipid having at least one fatty acid chain of carbon chain length $C_{12}$ to $C_{24}$, wherein the all-cis-9,12,15-octadecatrienoic acid is not attached to the phospholipid, and the phospholipid comprises:
            a head group selected from the group consisting of a choline, an ethanolamine, a serine, an inositol, a PEG molecule, a cell-penetrating peptide, and an antibody, and
            a tail group comprising at least one poly-unsaturated fatty acid;
      a beta-glucan, wherein the beta-glucan is derived from oat;
      cholesterol, which is integral to the bilayer; and
      doxorubicin, which is encapsulated within the internal compartment;
      wherein the therapeutic liposome has a diameter in a range of 130 nm to 1.5 µm.

8. The method of claim 7, wherein the therapeutic liposome further comprises a second active agent which is an anthracycline selected from the group consisting of epirubicin, daunorubicin, idarubicin, valrubicin, and mitoxantrone, wherein the second active agent is encapsulated within the internal compartment.

9. The method of claim 7, wherein the beta-glucan is a linear or a branched (1,3) beta glucan, or a linear or a branched (1,3)(1,4)beta-glucan, or a combination thereof.

10. The method of claim 7, wherein the therapeutic liposome is administered to the subject every 10-30 days.

11. The method of claim 7, wherein the therapeutic liposome is administered at a rate of 0.2 mg/min-2 mg/min.

12. The method of claim 10, wherein a cumulative dose does not exceed 400-600 mg/m$^2$.

13. The method of claim 7, wherein the cancer is at least one selected from the group consisting of an ovarian cancer, a multiple myeloma, a sarcoma, a colorectal cancer, and a breast cancer.

* * * * *